United States Patent [19]
Myers

[11] Patent Number: 5,865,081
[45] Date of Patent: *Feb. 2, 1999

[54] ANTI-ROLL RAKE

[75] Inventor: John Charles Myers, South Bend, Ind.

[73] Assignee: Sakura Finetek U.S.A., Inc., Torrance, Calif.

[*] Notice: This patent issued on a continued prosecution application filed under 37 CFR 1.53(d), and is subject to the twenty year patent term provisions of 35 U.S.C. 154(a)(2).

[21] Appl. No.: 410,727

[22] Filed: Mar. 27, 1995

[51] Int. Cl.⁶ .................................................. B26D 7/06
[52] U.S. Cl. ............................... 83/149; 83/112; 83/150; 83/154; 83/165; 83/385; 83/698.11; 83/915.5
[58] Field of Search ................................... 83/915.5, 170, 83/171, 870, 874, 150, 154, 161, 456, 453, 464, 465, 915, 915.3, 156, 422, 436.3, 436.4, 436.45, 698.31, 698.51, 698.11, 698.71, 79, 81, 83, 101, 112, 385, 165, 149, 162

[56] References Cited

U.S. PATENT DOCUMENTS

| | | | |
|---|---|---|---|
| D. 326,860 | 6/1992 | Holbl | D15/140 |
| 1,091,655 | 3/1914 | Hampp | 83/465 X |
| 1,153,498 | 9/1915 | Keller | 83/436.4 X |
| 1,954,032 | 4/1934 | Wood | 83/465 X |
| 1,976,865 | 10/1934 | Van Berkel | 83/96 |
| 2,274,626 | 2/1942 | Van Berkel | 83/96 |
| 2,384,732 | 9/1945 | Ocenasek | 83/465 X |
| 2,647,439 | 8/1953 | Roofe et al. | 83/915.5 X |
| 2,662,445 | 12/1953 | Jacoby, Jr. | 83/915.5 X |
| 2,957,379 | 10/1960 | Sidebotham, Sr. et al. | 83/436.3 X |
| 3,068,918 | 12/1962 | Smith | 83/436.45 X |
| 3,191,476 | 6/1965 | McCormick | 83/915.5 X |
| 3,227,020 | 1/1966 | Zeytoonian | 83/915.5 X |
| 3,293,966 | 12/1966 | McCormick | |
| 3,599,523 | 8/1971 | Pickett | 83/412 |
| 3,699,830 | 10/1972 | Pickett | 83/13 |
| 3,723,226 | 3/1973 | Pfohler | 83/915.5 X |
| 3,733,948 | 5/1973 | Pickett | 83/98 |
| 3,958,475 | 5/1976 | Zapomel | 83/112 |
| 4,009,741 | 3/1977 | Zimmerman | 144/41 |
| 4,024,779 | 5/1977 | Taugner et al. | 83/165 |

(List continued on next page.)

FOREIGN PATENT DOCUMENTS

| | | |
|---|---|---|
| 4307 738 A1 | 9/1993 | Germany . |
| 49-133685 | 3/1973 | Japan . |
| 51-134488 | 11/1976 | Japan . |
| 55-142237 | 11/1980 | Japan . |
| 5-273094 | 10/1993 | Japan . |
| WO 93/05936 | 4/1993 | WIPO . |
| WO 94/28390 | 12/1994 | WIPO . |

OTHER PUBLICATIONS

Surgipath Medical Industries, "AS 620 Cyotome" (date unknown; admitted prior art).
SLEE Tecknik GmbH, "Cryostat MTE" (c.1990).
Carl Zeiss/Fisher Scientific, "Carl Zeiss Slide Stainers", Microtomes and Cryostats (Jan. 1994).
Fisher Scientific, "Clinical Cryostats HM 505 Series from Carl Zeiss" (Apr. 1992).
Carl Zeiss, Inc. "Microscope and Histology Product Line" (Oct. 1992).
Hacker Instruments Inc., "Cryostats to rely on " (Spring 1991).
Miles, Inc., "Operating Manual, TISSUE–TEK Microtome/Cryostat" (1976, 1986, Jun. 1994).

*Primary Examiner*—Rinaidi I. Rada
*Assistant Examiner*—Boyer Ashley
*Attorney, Agent, or Firm*—Baker & McKenzie

[57] ABSTRACT

An apparatus for cutting thin tissue sections using an anti-roll rake. The anti-roll rake comprises a rake head for engaging the cut tissue section and leading it away from the specimen block without rolling. The rake head is hingedly mounted to a mounting surface in the cutting instrument by way of a linkage assembly in order to provide freedom of movement between the various operational and non-operational positions.

22 Claims, 8 Drawing Sheets

U.S. PATENT DOCUMENTS

| | | | |
|---|---|---|---|
| 4,338,836 | 7/1982 | Kuchler . | |
| 4,433,599 | 2/1984 | Mundus et al. | 83/112 X |
| 4,472,989 | 9/1984 | Endo | 83/162 |
| 4,700,600 | 10/1987 | Pickett | 83/165 |
| 4,997,017 | 3/1991 | Dobbie | 144/128 |
| 5,050,470 | 9/1991 | Ward | 83/915.5 X |
| 5,092,210 | 3/1992 | Dern | 83/698.11 |
| 5,099,735 | 3/1992 | Kempe et al. | 83/915.5 X |
| 5,267,496 | 12/1993 | Roach et al. | 83/465 X |
| 5,361,666 | 11/1994 | Kensrue | 83/465 X |

ANTI-ROLL RAKE

BACKGROUND OF THE INVENTION

The present invention relates to an anti-roll rake device for use in conjunction with a device such as a microtome for cutting frozen samples and to prevent the cut samples from rolling.

In the medical field it is often desired to cut thinly sliced tissue samples for testing or viewing under a microscope. Various devices are known for making such samples, such as razor blades and more specialized instruments. Accurate sample cuts are often required and typically require the use of a microtome instrument.

Various forms of microtomes are known. In general, a microtome is an instrument for cutting thin tissue sections. The sections can be stained for later study under a microscope. One such microtome is the TISSUE-TEK® Microtome/Cryostat which was manufactured by Miles Inc., Diagnostic Division, Elkhart, Ind. In such a microtome, the tissues to be sampled are prepared for cutting by being embedded in a supportive matrix and then frozen solid. The frozen matrix and embedded tissue are cut with a sharp blade to produce thin sections, which can then be stained and placed on a microscope slide and subsequent viewing under a microscope.

The nature of the slicing process causes the cut section to roll tightly almost immediately after leaving the sharp edge of the cutting blade. Even with the various known anti-roll devices, the cut section still has a structural memory of the rolling, and a tendency to roll or curl after removal from the device.

Various anti-roll devices are known. One such apparatus is an anti-roll plate, as illustrated in U.S. Pat. No. 4,472,989. The anti-roll plate may be a plastic surface. The anti-roll plate is positioned adjacent to the surface of the blade, with a slight gap therebetween. The sample section is expected to pass through the gap between the blade and the anti-roll plate. The gap between the anti-roll plate and blade typically is set to correspond to the thickness of the sample piece to be cut. If the thickness of the sample piece is increased, the gap must also be increased. In other anti-roll plates, the gap is situated between the tissue block to be cut and the plate.

The known anti-roll plates and corresponding techniques suffer the disadvantage of a high proportion of cut sections which get caught on the anti-roll plate, or elsewhere within the gap between the blade and therefore become tainted or unusable. A further disadvantage is that the selection of the width of the gap between the anti-roll plate and blade requires skill and discretion. In addition, dexterity is required to accurately remove the cut section.

Yet a further disadvantage of the anti-roll plate is that the cut tissue section tends to curl or roll after the anti-roll plate is lifted in order to gain access to the cut section. In addition, in typical commercial embodiments, the anti-roll plate is mounted in front of the blade holder and tends to reduce the freedom of access to the cut section. This impairs the ability to readily access the cut section with a glass microscope slide.

Another known technique and apparatus for countering the tendency of thinly sliced tissue sections to roll or curl makes use of a brush. The brush is positioned to catch the leading edge of a tissue section as it passes the blade. This suffers similar disadvantages as discussed above, including requiring operator dexterity and therefore being highly technique dependent. In addition, the operator typically is required to manually guide the brush, during the cutting process. Furthermore, if the brush drags on the cutting surface of the blade, some of the brush bristles may be cut off, potentially contaminating the tissue sample, dulling the blade and reducing the brush size.

Furthermore, the known devices and techniques suffer the disadvantages of requiring slow cutting speeds in order to prevent rolling.

Other such anti-roll devices, which rely on the use of gaps between the blade and device are discussed in U.S. Pat. No. 4,024,779. These devices suffer the same disadvantages as those described above.

It is readily appreciated that there is a substantial need for an anti-roll device that does not rely on operator dexterity or guiding the sample slice between a blade or tissue sample and an anti-roll device.

SUMMARY OF THE INVENTION

The present invention alleviates to a great extent the disadvantages of the known anti-roll devices by providing an anti-roll rake in which the anti-roll rake engages the forward portion of cut sample section and guides it away from the specimen block, such as a frozen matrix, from which it is cut.

In particular, the anti-roll rake includes a rake head for engaging the cut sample slice. The rake head is mounted, preferably flexibly, to a linkage member, which in turn is hingedly linked to a portion of the cutting instrument, such as a microtome. The rake head can be flipped about the hinge mechanism between an operational and non-operational position. In use, the rake head is flipped into an operational position in which it is adjacent to or contacting a specimen block from which the section is cut. A blade begins the cut and the leading edge of the section slice engages a surface of the rake head. Typically, the section slice will immediately curl after being cut, in the absence of an anti-roll device. The curling leading edge engages the rake head, such as by action of friction and/or surface tension. As the blade proceeds with the cutting process, the rake head automatically moves away from the specimen block at a rate approximately equal to the linear motion of the blade. After the section is completely cut from the specimen block, the rake head may be flipped away from the operational position, so that it lifts the attached cut section. The cut section may then be easily applied to a microscope slide.

In a microtome, the specimen block may be mounted to a chuck. In use, the blade and chuck move relative to each other such that the blade moves linearly through the length of the mounted specimen block, causing a thin section of the specimen block to be cut. Preferably, the blade remains stationary and the chuck moves down past the blade. As the chuck and blade move relative to one another, the rake head preferably engages an extender channel and moves generally linearly away from the chuck and specimen block, along the extender channel. In so moving, the rake head extends the cut section linearly, preventing rolling. Likewise, when the head is raised away from the extender channel, into a non-operational position, after the cut is completed, the cut specimen does not roll as it preferably dangles down from the rake head.

The rake head preferably is flexibly mounted allowing the rake tips to be automatically set when in contact with the specimen block and extender channel.

In addition, the linkage member preferably is mounted to the chuck. This allows the rake head to be flipped clear of the chuck and blade assembly, allowing maximum operator freedom of motion and vision for slice pick-up and blade positioning. As little operator dexterity or discretion is required, speed of cutting has a reduced effect on ease of use.

BRIEF DESCRIPTION OF THE DRAWINGS

The above and other objects and advantages of the invention will be apparent upon consideration of the following detailed description, taken in conjunction with the accompanying drawings in which like reference characters refer to like parts throughout and in which.

DETAILED DESCRIPTION OF THE INVENTION

Figure 1:
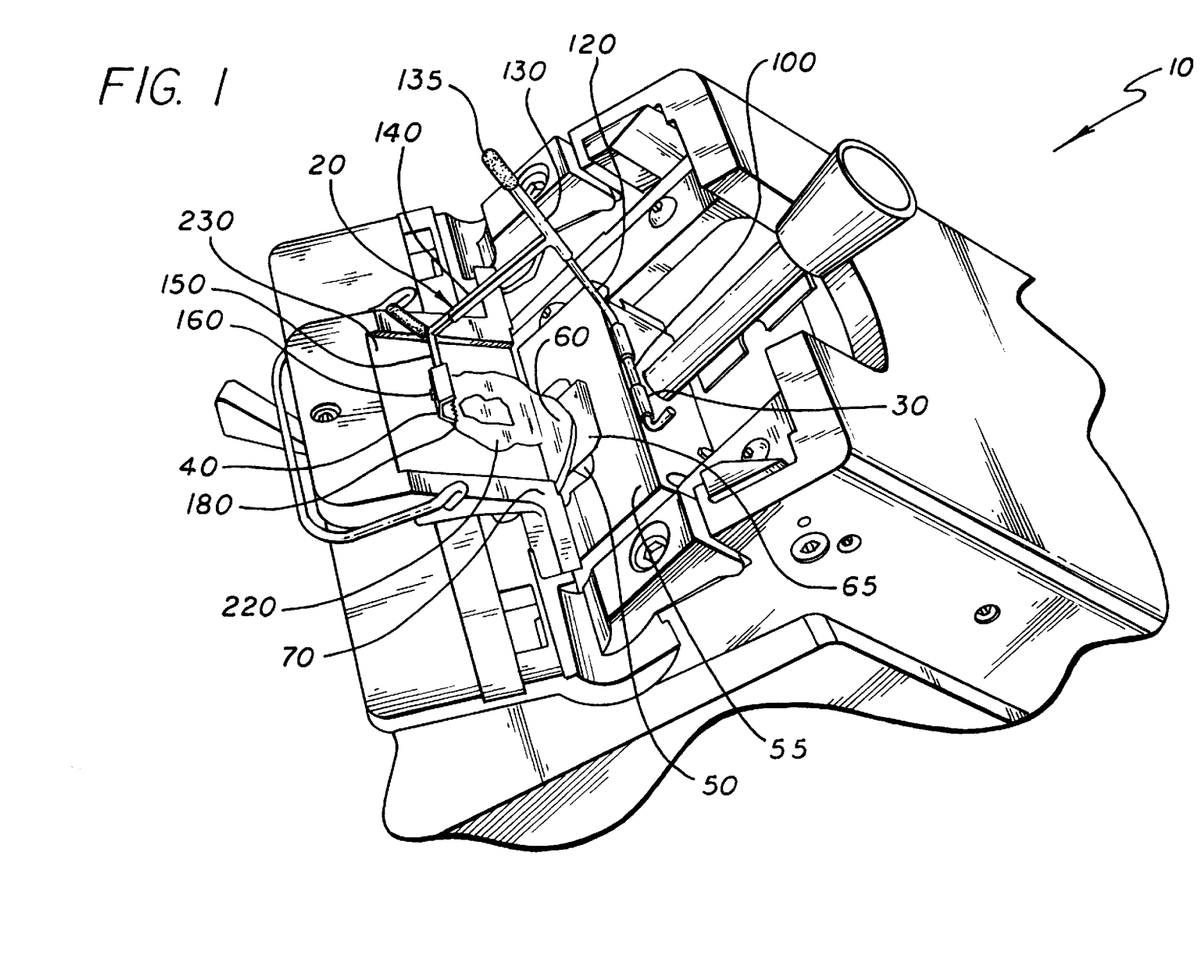
FIG. 1 is a perspective view of the microtome including anti-roll rake in accordance with the present invention.

FIG. 1 provides a perspective view of a microtome 10 constructed in accordance with the present invention. The anti-roll rake 20 is mounted to the microtome 10 by way of hinge 30. The hinge 30 may be situated on any part of the microtome 10 provided that the rake head 40 of the anti-roll rake 20 can be moved from an operational to a non-operational position.

Figure 2:
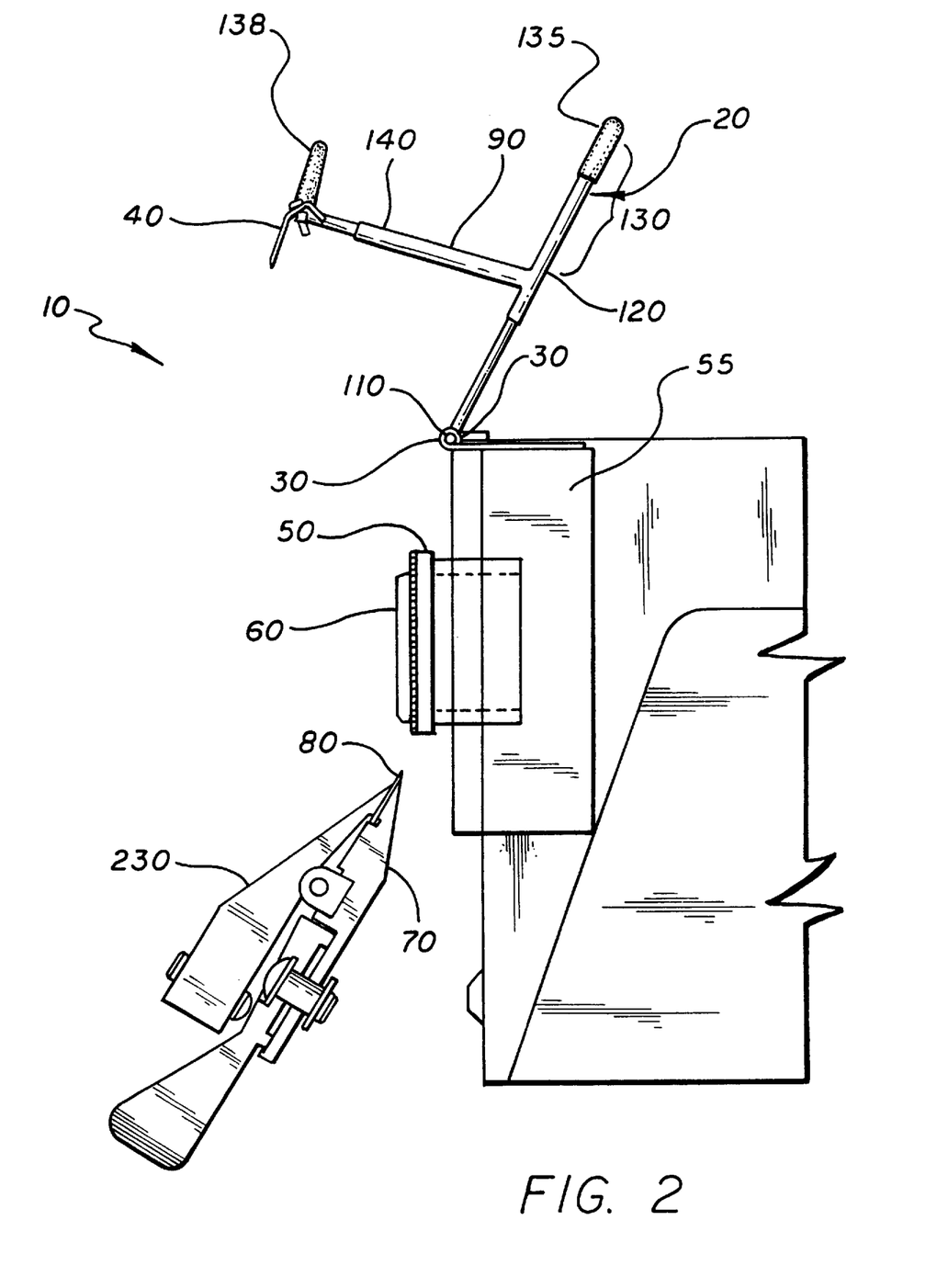
FIG. 2 is a side view of the microtome with anti-roll rake of FIG. 1, with the anti-roll rake in an elevated position.
Figure 9:
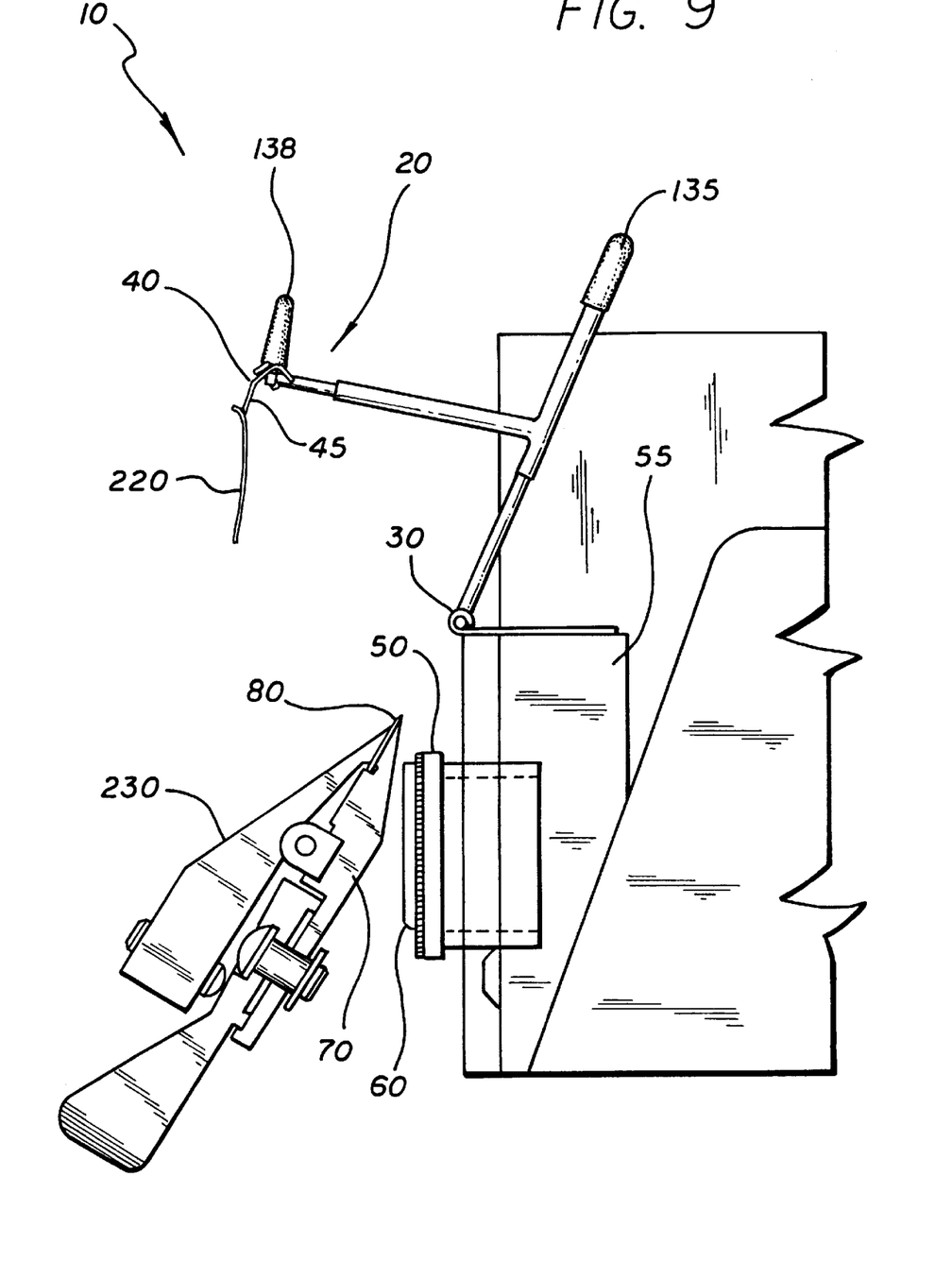
FIG. 9 is a side view of the microtome with anti-roll rake of FIG. 1, after making a section cut with the anti-roll rake in an elevated position.

In the non-operational position, the rake head 40 is spaced apart from the working parts of the microtome 20, as illustrated in FIGS. 2 and 9. For example, the working parts of the microtome may include a chuck 50 for holding a specimen block 60. They may also include the blade holder 70 and associated blade 80.

The chuck 50 is mounted in the microtome housing. In a preferred embodiment, the chuck 50 is mounted on a mounting surface 55, such as a movable chuck housing 55. Preferably, the mounting surface 55 is movable in a single plane, in a linear fashion, such as up and down. Alternatively, the chuck 50 and chuck housing 55 may be stationary and the blade holder 70 may move in such a linear fashion, in a single plane. In still another alternative embodiment, both the blade holder 70 and the chuck housing 55 may be movable in such a linear fashion. In each of these embodiments, a generally linear movement between the specimen block 60 and blade 80 is desired, such that the blade 80 can make a thin section slice of the block 60, with a generally uniform thickness. In other words, the blade 80 shaves a thin slice from specimen block 60 by being guided in a linear fashion past the specimen block 60.

The specimen block 60 preferably includes a tissue sample, which is embedded in a supportive matrix. Any material may be used for a supportive matrix which will allow a tissue specimen to be embedded and a section to be cut. Examples of such embedding materials are polymeric materials, paraffin or wax. Preferably, when a cut is made, tissue sample/matrix also is frozen solid. The solid tissue sample and matrix may be inserted into a specimen block holder 65 and subsequently inserted into the chuck 50. After the specimen block 60 is formed, it is fixedly mounted into the chuck 50, such that is held in place during the cutting process.

Any type of blade holder 70 can be used, as long as it can hold the blade 80 fixed in place relative to the blade holder 70 under the stresses of the cutting operation. In the example illustrated in FIGS. 1–4 and 7–9, the blade holder 70 holds the blade at an angle such that the blade will cut the specimen block 60 when it moves upwards across the face of the specimen block 60, or when the specimen block 60 moves down across the blade. In either alternative, a relative movement of the specimen block 60 with the blade 80 is achieved whereby they move linearly past each other.

The hinge 30 illustrated in FIGS. 1–3 and 7–9 is preferably mounted above the chuck 50 on the chuck housing 55 and moves along with the chuck housing 55 and attached chuck 50 when the chuck housing is positioned or otherwise moved. Alternative mounting surfaces for the hinge 30 also can be selected, as long as the rake head 40 can be properly positioned for engaging a cut section. In the non-operational position illustrated at FIG. 2, the position of the hinge 30 allows the anti-roll rake 20 and its rake head 40 to be raised out of the way of the blade 80 as well as the specimen block 60. This allows for easy positioning of the blade 80 with respect to the specimen block 60. In addition, the position illustrated in FIG. 9 allows for easy access to the section 220, such as with a microscope slide.

The anti-roll rake 20 and rake head 40 are hingedly mounted through a linkage assembly 90. In the preferred embodiment, the linkage assembly 90 includes elongated members 100, 120, 130, 140. One such member 100 couples with a hinge receiving element 110 in order to enable the anti-roll rake 20 to pivot. Together, member 100 and hinge receiving element 110 form the hinge 30 illustrated in the figures. However, any type of hinge which can provide movement of the anti-roll rake 20 between the various operational positions and the non-operational positions may also be used. In the preferred embodiment, a second linkage member 120 extends perpendicularly from the first leg 100, providing an radial distance between the mounting surface 55 and the rake head 40. The second member 120 alternatively may have a gripper section 130, such as at its end opposite the hinge 30. The gripper section 130 includes an extension which may be capped by a gripper surface 135, such as a cap. The cap may be constructed of any substance such as rubber or a plastic. Other gripper sections and caps 138 can be placed at other locations on the linkage assembly 90. Between the two ends of the second member 120, a third member 140 may extend axially therefrom. This third member 140 provides the requisite axial distance from the position at which the anti-roll rake is mounted to the hinge 30 and the desired positioning with respect to the section block 60. The rake head 40 is mounted off of this third member 140. In the illustrated embodiment, a fourth member 150 provides the actual mounting surface. In the illustrated embodiment, this fourth member 150 extends in a direction generally parallel to the hinge 30 and mounting surface 55 and perpendicular to the third leg 140.

The rake head 40 may be mounted using any known mounting device. Preferably, the mounting device provides some flexibility such that the rake head 40 can pivot, when in use. An exemplary attachment device is a threaded screw 160 which extends through an aperture 170 defined in the rake head and through an aperture defined in the fourth leg 150, thereby pivotally attaching the rake head 40 to the fourth leg 150.

The rake head 40 also includes a leading edge 180. Preferably, the leading edge has a jagged, notched or serrated profile, in order to enhance its ability to engage a cut section.

Figure 3:
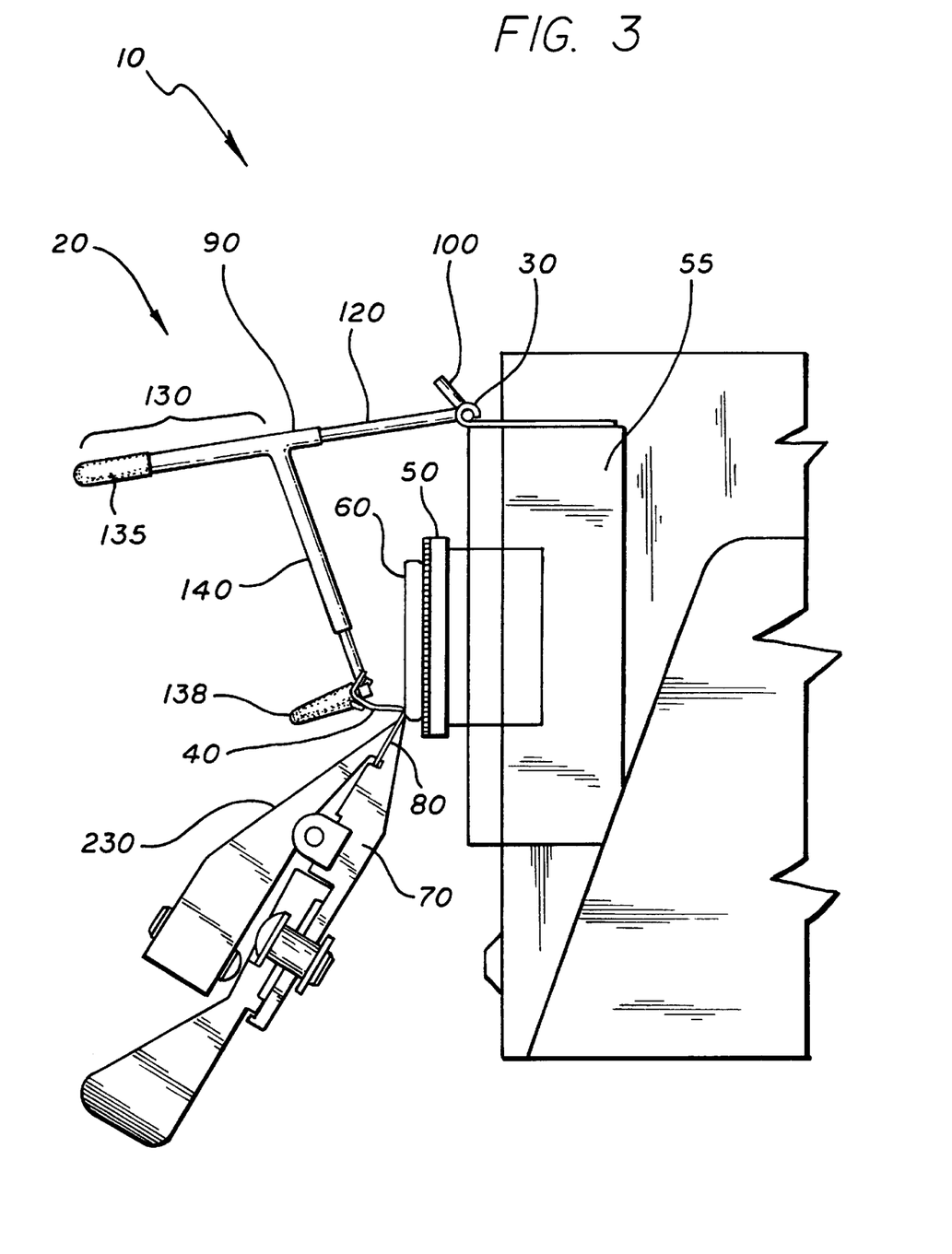
FIG. 3 is a side view of the microtome with anti-roll rake of FIG. 1, with the anti-roll rake lowered into operational position.

In the initial operational position, the anti-roll rake 20 is pivoted or rotated about hinge 30 such that the rake head 40 is in position to receive and engage a cut sample section. As the anti-roll rake 20 is moved into the initial operational position, its attached rake head 40 rotates forward and down, preferably until the rake tip 180 is in contact with the bottom of the specimen block 60, which is mounted in chuck 50. Preferably, the rake tip 180 contacts the bottom 1/16" of the specimen block 60. This can readily be accomplished in the preferred embodiment by moving the chuck 50 and mounted specimen block 60 to a position in which the bottom edge of the specimen block 60 is above, or aligned with the cutting edge of blade 80, as illustrated in FIGS. 2 and 3.

In operation of the preferred embodiment, in which the chuck housing 55 and mounted chuck 50 are moveable and the blade holder 70 and mounted blade 80 are stationary, the chuck 50 is moved downward, past blade 80 in order to slice off a portion of the specimen block 60 in order to create a sample section 220. In this process, as the leading edge 200 of the section is cut, and moves past the blade 80, the leading edge 200 and the rake tip 180 pass the edge of the blade 80.

Figure 4:
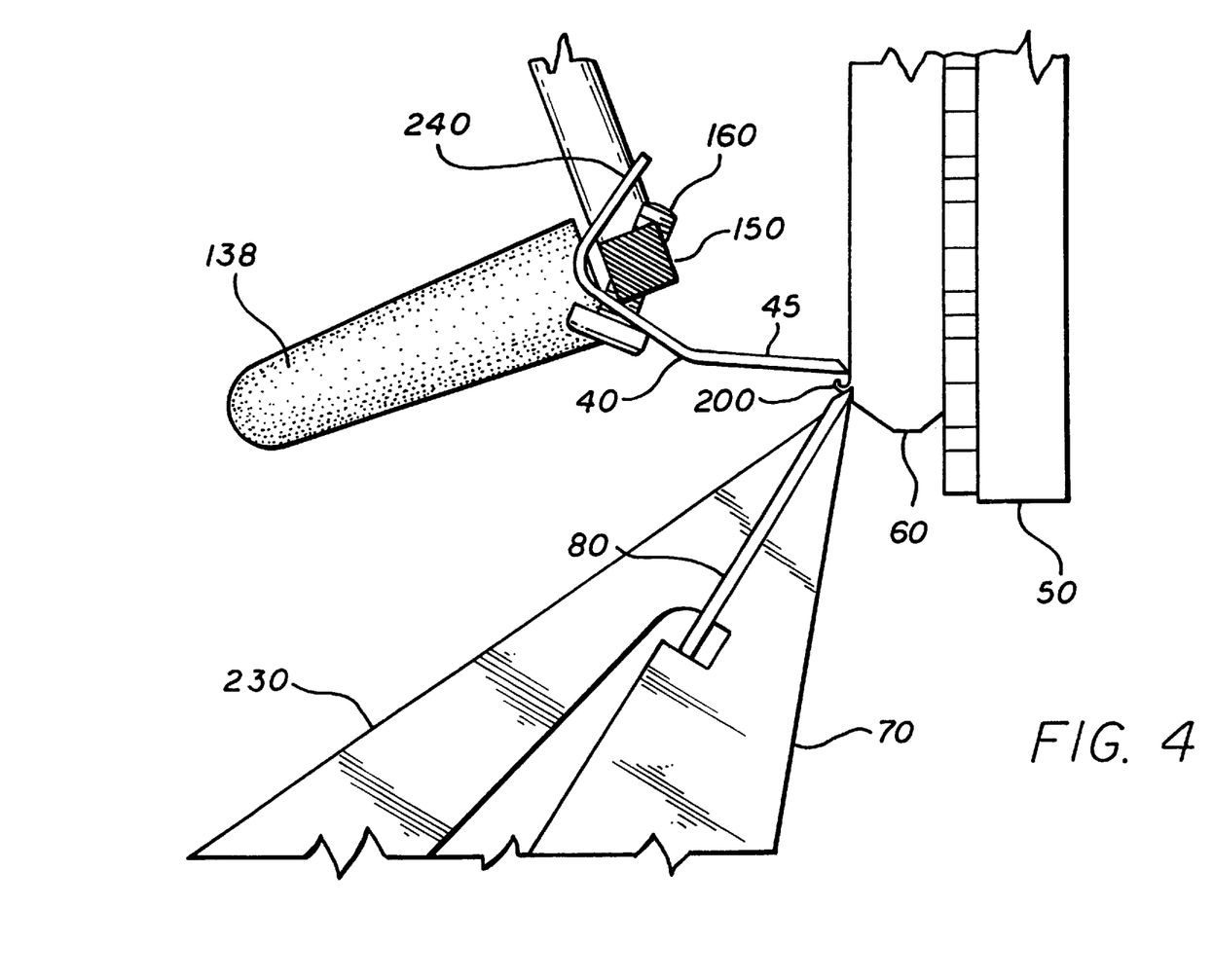
FIG. 4 is a detailed side view of the microtome with anti-roll rake of FIG. 3, at the beginning of making a section cut.
Figure 5:
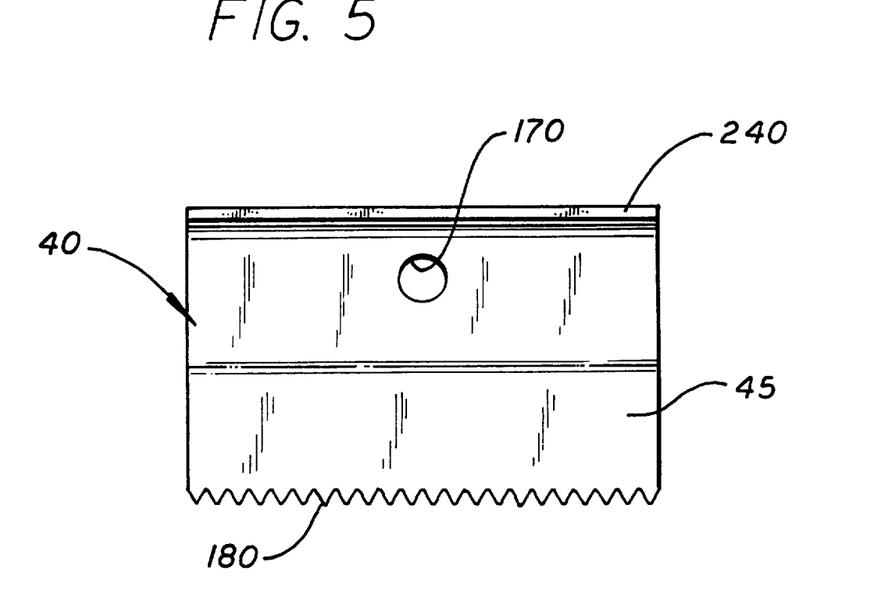
FIG. 5 is a front view of the anti-roll rake head of the present invention.
Figure 6:
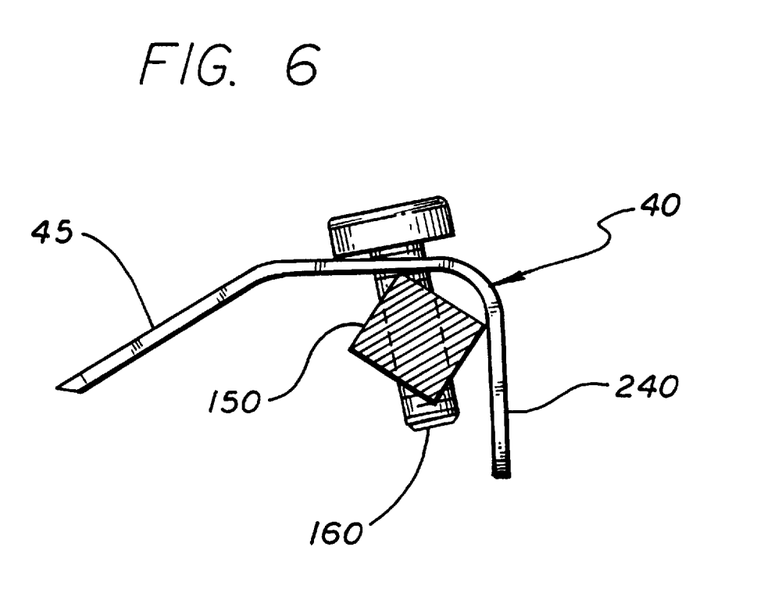
FIG. 6 is a side view of the anti-roll rake head of the present invention.

The rake head 40 may first engage the cut section 200, for example, in two different ways. As is illustrated in FIG. 4, the leading edge 200 of the section may curl. When the curling leading edge 200 contacts the outer surface 45 of rake head 40, it is engaged by the rake head. Likewise, when the leading edge 200 contacts the rake tip 180, it is engaged by the rake head.

In the illustrated embodiment, the rake head 40 leads the leading edge 200 of specimen 220 down an extender channel 230. The extender channel 230 is a surface providing support for the rake head 40 and section 220. In the illustrated embodiment, the extender channel 230 is located on an outer surface of blade holder 70. The rake head 40, preferably leads or pulls the leading edge 200 of the section 220 at approximately the linear velocity of the blade 80 with respect to the specimen block 60.

In so moving, the rake head extends the section 220 away from the chuck 50 and specimen block 60. This preferably linear movement prevents rolling.

The operation of the anti-roll rake 20 and microtome 10 is illustrated sequentially in FIGS. 2, 3, 7, 8, 1 and 9. Following the sequence of operation, it is seen that the anti-roll rake 20 optionally starts in a raised position. Then the anti-roll rake is rotated into its starting position, adjacent the lower edge of specimen block 60. Preferably, there is a small distance between the bottom edge of the specimen block 60 and the tip 180 of the rake head 40. The chuck 60 also is moved down into its starting position in which the blade 80 is in close proximal relation to the bottom surface of the specimen block 60.

Figure 7:
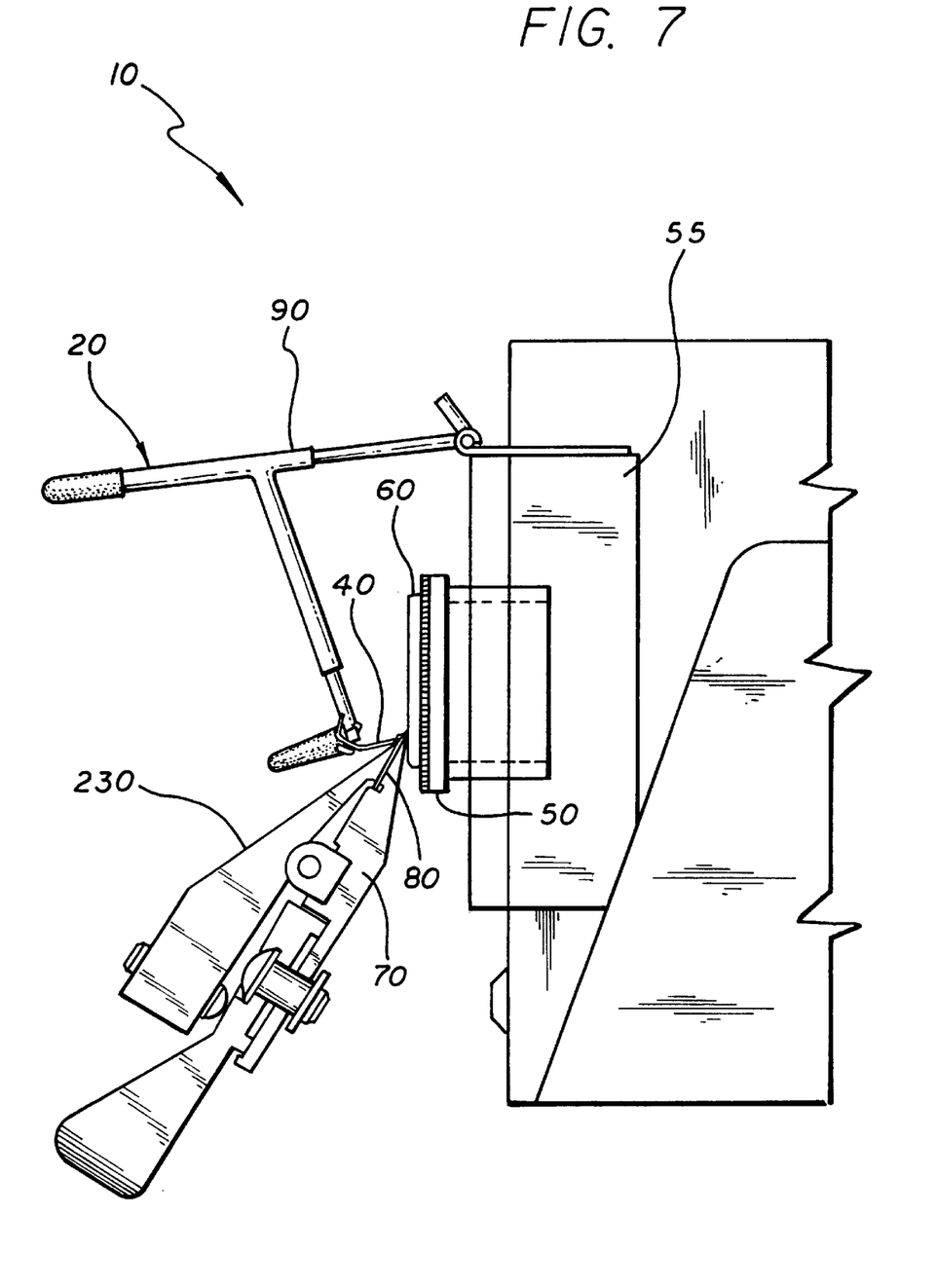
FIG. 7 is a side view of the microtome with anti-roll rake of FIG. 1, while making a section cut.
Figure 8:
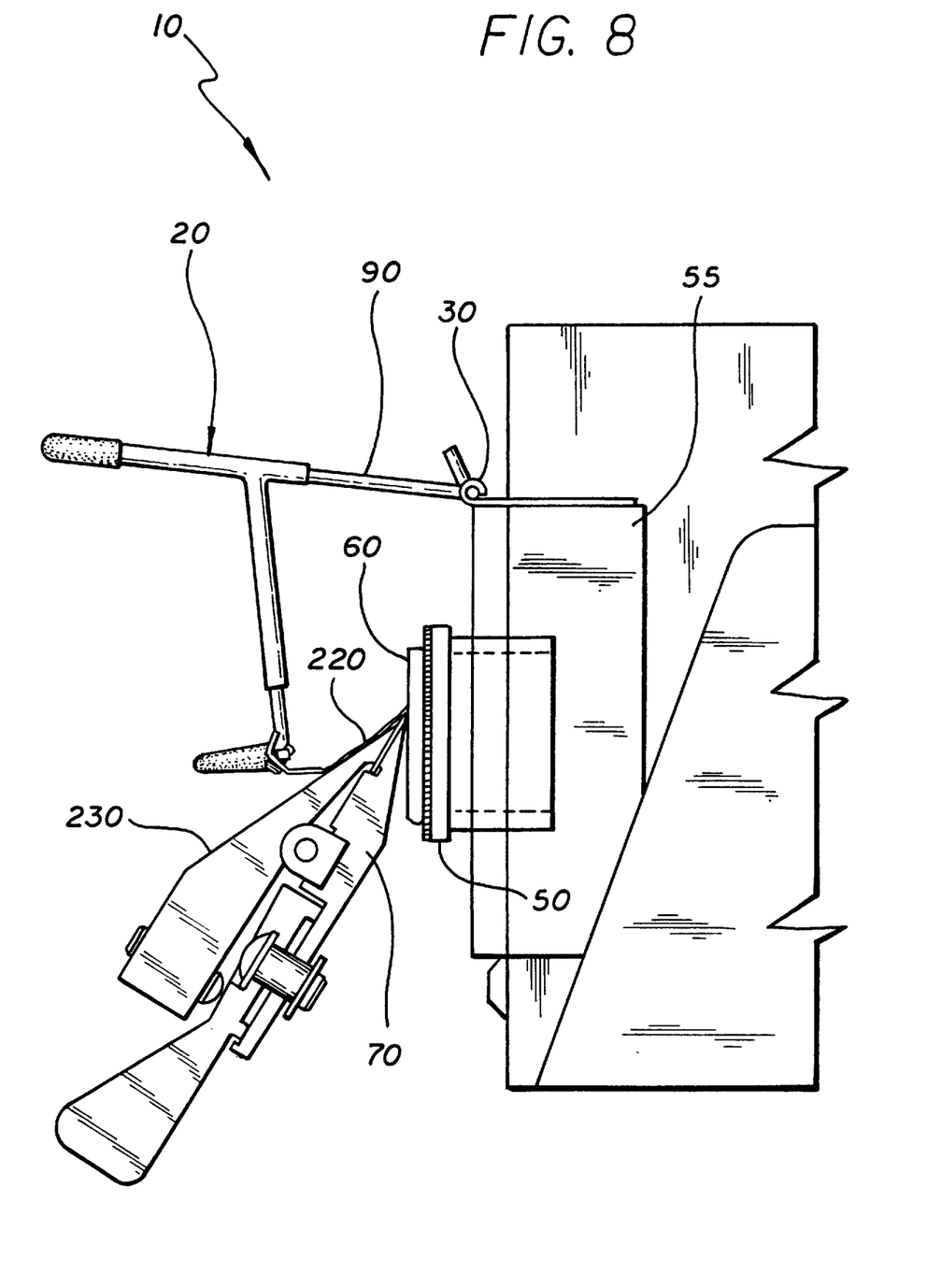
FIG. 8 is a side view of the microtome with anti-roll rake of FIG. 1, in the middle of making a section cut.

The initial cut is illustrated in FIG. 4, which shows the curling leading edge 200 of the cut specimen 220. FIG. 7 shows the initial movement of the anti-roll rake 20, as well as chuck 50 and chuck housing 55. The chuck 50 is moved linearly relative to blade 80, causing the specimen block 60 to move relatively downwards with respect to blade 80. The leading edge 180 of rake head 40 is adjacent the blade holder 70. FIGS. 1 and 8 illustrate an intermediate stage of the cutting process. Chuck 50 has been moved downwards such that blade 80 is in the middle portion of specimen block 60. The section 220 is shown being drawn, without rolling, over extender channel 230 by the rake head 40. The final phase, after completion of the cut, is illustrated in FIG. 9. There, the cut section 220 is shown dangling from raised anti-roll rake 20. A microscope slide (not shown) may be introduced in order to engage the section 220 and retrieve it from the anti-roll rake 20 and its rake head 40.

In a preferred embodiment, at the point where the rake head 40 begins advancing and pulling the leading edge 200 and section 220 through the extender channel, the top edge 240 of rake head 40 may be tapped by the operator, such as with a brush, rod or finger, in order to set the rake edge 180 into the edge 200 of section 220. This enhances the adhesion between the section 200 and the rake head 40. When the anti-roll rake assembly 20 is rotated into its non-operational position, the specimen will readily adhere and hang generally vertically from the rake head into free space. This increases the likelihood that a useable section will be obtained. The adhesion of the leading edge 200 of section 220 is also promoted because the rake head 40 is pivotally mounted. This gives the freedom of movement in order to promote a proper setting with the rake edge of the section 200.

In an alternative embodiment, after the leading edge 200 of section 220 is engaged by the edge 180 of rake head 40, the slicing process may be stopped and the section 200 can be held in place manually with a brush. The anti-roll rake 20 can be rotated back into its non-operational position and the section cutting can then continue.

Other embodiments of the anti-roll rake 20 of the present invention are also envisioned. The anti-roll rake 20 may be mounted in any fashion to the cutting apparatus, as long as it can be positioned in order to engage the leading edge of a cut specimen and lead it away from the specimen block from which it is cut. Accordingly, in other embodiments the linkage members are arranged in different fashions, so as to enable the rake head 40 to be positioned properly and move between the various operational and non-operational positions.

Thus, it is seen that a microtome apparatus having an anti-roll rake is provided. One skilled in the art will appreciate that the present invention can be practiced by other than the preferred embodiments which are presented for purposes of illustration and not of limitation, and the present invention is limited only by the claims which follow.

What is claimed is:

1. An apparatus for cutting a section from a block of material comprising:
   a mounting housing retaining said block of material;
   a cutting instrument;
   a cutting instrument housing retaining the cutting instrument, the cutting instrument housing being translatable relative to the mounting housing to cut the section from said block of material;
   an anti-roll rake assembly, including:
      a linkage assembly hingedly connected to the mounting housing wherein the linkage assembly comprises a first elongated member hingedly connected to the mounting housing, and a second elongated member connected in fixed angular relation to the first elongated member, the second elongated member having a first end connected to the first elongated member and a second end, wherein the rake head is connected at the second end; and a discrete rake head including a plate member mounted on the linkage assembly.

2. The apparatus of claim 1 wherein the rake head is pivotally connected to the second elongated member.

3. The apparatus of claim 1 wherein the cutting instrument housing includes a planar guide surface not part of the cutting instrument and the linkage assembly directs the rake head into contact with the guide surface and directs the rake head along the guide surface away from the block of material as the section is being cut from said block of material.

4. The apparatus of claim 3 wherein the guide surface of the cutting instrument housing comprises a generally planar surface.

5. The apparatus of claim 3 wherein the cutting instrument comprises a blade.

6. The apparatus of claim 1 further comprising a guide surface on the cutting instrument housing for guiding the rake head away from the block of material while the section is being cut from the block of material.

7. An apparatus for cutting a section from a block of material comprising:

a mounting housing retaining said block of material;

a cutting instrument;

an anti-roll rake assembly, including:

a linkage assembly hingedly connected to the mounting housing; and a discrete rake head including a plate member mounted on the linkage assembly; and a cutting instrument housing retaining the cutting instrument, the cutting instrument housing being translatable relative to the mounting housing to cut the section from said block of material wherein the cutting instrument housing comprises a planar guide surface means on the cutting instrument housing for directing the rake head away from the mounting housing as long as the section is being cut from said block of material wherein the guide surface means is not a part of the cutting instrument.

8. The apparatus of claim 7 wherein the guide surface means includes a substantially planar engagement surface for receiving the rake head.

9. The apparatus of claims 1 or 7 wherein:

the discrete rake head further comprises a leading edge for engaging the section as it is being cut; and the leading edge includes an irregular profile for enhancing the engagement of the discrete rake head with the section.

10. The apparatus of claims 1 or 7 wherein the linkage assembly includes:

a hinge means for moving the rake head from a non-operational position in which the rake head does not contact the block of material to an operational position in which the rake head contacts an edge of the block of material retained by the mounting housing.

11. The apparatus of claims 1 or 7 wherein:

said plate member of the rake head includes a top side and a bottom side;

said linkage assembly includes a positioning means for positioning the bottom side of the plate member of the rake head in contact with the section while it is being cut from said block of material.

12. The apparatus of claims 1 or 7 wherein the discrete rake head is pivotally mounted on the linkage assembly using a fastener.

13. The apparatus of claims 1 or 7, wherein said linkage assembly includes means for movably directing the rake head between engagement with the section while the section is being cut from said block of material and a retrieval position away from said block of material.

14. The apparatus of claims 1 or 7 further comprising a fastener, wherein the discrete rake head is mounted on the linkage assembly with the fastener.

15. The apparatus of claim 14 wherein:

the fastener includes a threaded screw;

the plate member of the discrete rake head defines an aperture;

the linkage assembly includes a rake head mounting member defining an aperture; and the threaded screw extends through the aperture defined in the rake head and the aperture defined in the rake head mounting member of the linkage assembly.

16. The apparatus of claim 14 wherein:

the fastener includes a post member;

the plate member of the discrete rake head defines an aperture;

the linkage assembly includes a rake head mounting member defining an aperture; and the post member extends through the aperture defined in the rake head and the aperture defined in the rake head mounting member of the linkage assembly.

17. An apparatus for cutting a section of a block of material comprising:

cutting means for cutting said section from said block of material;

cutting means housing mounting said cutting means in movable relation to said block of material;

a rake head including a plate member having an engaging surface;

rake head mounting means for positioning said rake head so that said engaging surface of said plate member contacts said block of material and for moving said rake head and said section away from said block of material while the section is being cut from said block of material; and wherein said cutting means housing includes a guide channel means for engaging said rake head and directing it away from said block of material while said section is being cut, the guide channel means including a generally planar surface.

18. The apparatus of claim 17 wherein the guide channel means includes an exterior guide surface.

19. An apparatus for cutting a section from a block of material, the apparatus including a mounting housing retaining said block of material, and a cutting instrument, the apparatus comprising:

a cutting instrument housing retaining the cutting instrument, the cutting instrument housing being translatable relative to the mounting housing retaining said block of material to cut the section from said block of material;

an anti-roll rake assembly, including:

a rake head means for directing said section away from the block of material, said rake head means including a plate member;

a linkage assembly means hingedly connected to the mounting housing for mounting the plate member of the rake head means and for directing the plate member into an engaging relation with said section while it is being cut from said block of material, and for guiding the plate member away from the block of material as the mounting housing and the cutting instrument housing move relative to one another as said section is being cut from said block of material.

20. The apparatus of claim 19 further comprising a fastener wherein the plate member is pivotally mounted on the linkage assembly means with the fastener.

21. The apparatus of claim 19 wherein the cutting instrument housing includes an exterior guide surface.

22. The apparatus of claim 19 wherein the linkage assembly means comprises at least one elongated member hingedly connecting the rake head means to the mounting housing.

* * * * *